US012594099B2

(12) United States Patent
Nelsen et al.

(10) Patent No.: US 12,594,099 B2
(45) **Date of Patent: *Apr. 7, 2026**

(54) ROD REDUCTION INSTRUMENT FEEDBACK SYSTEM

(71) Applicant: NuVasive, Inc., San Diego, CA (US)

(72) Inventors: Christopher Nelsen, San Diego, CA (US); Robert German, San Diego, CA (US); Michael Serra, San Diego, CA (US)

(73) Assignee: Nuvasive Inc., San Diego, CA (US)

( * ) Notice: Subject to any disclaimer, the term of this patent is extended or adjusted under 35 U.S.C. 154(b) by 519 days.

This patent is subject to a terminal disclaimer.

(21) Appl. No.: 18/110,602

(22) Filed: Feb. 16, 2023

(65) Prior Publication Data

US 2023/0200865 A1    Jun. 29, 2023

Related U.S. Application Data

(63) Continuation of application No. 17/495,161, filed on Oct. 6, 2021, now Pat. No. 11,612,420.

(60) Provisional application No. 63/239,148, filed on Aug. 31, 2021.

(51) Int. Cl.
    *A61B 17/70*      (2006.01)
    *A61B 17/00*      (2006.01)

(52) U.S. Cl.
    CPC ...... *A61B 17/7086* (2013.01); *A61B 17/7076* (2013.01); *A61B 2017/00022* (2013.01)

(58) Field of Classification Search
    CPC . A61B 17/70; A61B 17/7074; A61B 17/7083; A61B 17/7086–7088; A61B 17/7091
    See application file for complete search history.

(56) References Cited

U.S. PATENT DOCUMENTS

| | | | |
|---|---|---|---|
| 9,198,698 B1 | 12/2015 | Doose et al. | |
| 11,051,861 B2 | 7/2021 | Morris | |
| 11,612,420 B2 * | 3/2023 | Nelsen ............... | A61B 17/7086 606/264 |
| 2008/0221626 A1 | 9/2008 | Butters et al. | |
| 2013/0072982 A1 * | 3/2013 | Simonson .......... | A61B 17/7083 606/267 |
| 2013/0090697 A1 * | 4/2013 | George .............. | A61B 17/7086 606/305 |
| 2013/0268007 A1 | 10/2013 | Rezach et al. | |

(Continued)

FOREIGN PATENT DOCUMENTS

WO        2021/108709 A1      6/2021

OTHER PUBLICATIONS

PCT International Search Report and Written Opinion for International Application No. PCT/US2021/053720, dated Jun. 3, 2022, 16 pages.

*Primary Examiner* — Eduardo C Robert
*Assistant Examiner* — Michelle C Green

(57)        ABSTRACT

Various implementations include rod reduction instruments, spinal fixation monitoring systems, and related methods. Certain implementations include a rod reduction instrument that is adapted for use with a spinal fixation system and includes a sensor configured to detect a load exerted by a rod reducer on a spinal rod, along with a reduction feedback system that provides an indicator of the load exerted by the rod reducer on the spinal rod.

17 Claims, 13 Drawing Sheets

(56)             References Cited

U.S. PATENT DOCUMENTS

| | | |
|---|---|---|
| 2019/0021769 A1 | 1/2019 | Lish |
| 2019/0069934 A1 | 3/2019 | Mickiewicz et al. |
| 2019/0150835 A1 | 5/2019 | Bae |
| 2020/0022733 A1* | 1/2020 | Benson ................. A61B 5/686 |
| 2020/0022739 A1* | 1/2020 | Benson ................ A61B 5/7275 |
| 2020/0069377 A1 | 3/2020 | Finley et al. |

\* cited by examiner

100

102

164

104

124

20

18

22

100

164

124

14

26

12

10

ROD REDUCTION INSTRUMENT FEEDBACK SYSTEM

PRIORITY CLAIM

This application claims the benefit of U.S. patent application Ser. No. 17/495,161 (filed Oct. 6, 2021), which itself claims priority to U.S. Provisional Application Ser. No. 63/239,148, filed on Aug. 31, 2021, each of which is incorporated herein by reference in its entirety.

TECHNICAL FIELD

This disclosure generally relates to medical devices. More particularly, the disclosure relates to the field of spinal surgery and spinal fixation devices.

BACKGROUND

Spinal fixation constructs are utilized to provide stability to the spine. Most often the fixation construct is used as an adjunct to fusion surgery during which adjacent vertebrae are prepared to facilitate bone growth between them. Because motion between the vertebrae tends to inhibit bone growth, the fixation constructs are employed to prevent motion so that bone can grow and achieve a solid fusion. When the position of one or more vertebrae must be adjusted to restore a more natural alignment of the spinal column, the fixation construct also serves to maintain the new alignment until fusion is achieved.

Fixation constructs of various forms are known in the art, of which, rod based fixation constructs are one of the most common. Typically a rod based construct includes multiple anchors that are coupled to a portion (e.g. the posterior elements) of two or more vertebrae and then connected by a fixation rod. The anchors further include a rod housing in which the fixation rod is captured and locked. The rod housing may be fixed, pivotably or rotatably coupled to the anchor portion and generally includes a pair of upstanding arms separated by a rod channel. When constructing the fixation construct the surgeon must align and seat the rod in the rod channel of each anchor, an undertaking that is generally referred to as "reduction." Reduction can be a challenge, particularly when one or more of the vertebrae to be connected are out of alignment with other vertebrae, and the reduction distance and force requirements can vary greatly from anchor to anchor. Conventional reduction procedures are heavily reliant upon the surgeon (or operator's) expertise in judging the load applied by each rod reducer on the spinal rod. In multi-level fixation procedures involving multiple vertebrae, it can be particularly challenging for the surgeon to determine which rod reducer(s) are properly loaded while engaged with the spinal rod.

SUMMARY

The needs above, as well as others, are addressed by embodiments of rod reduction instruments, spinal fixation monitoring systems, and related methods described in this disclosure. All examples and features mentioned below can be combined in any technically possible way.

Various implementations include rod reduction instruments, spinal fixation monitoring systems, and related methods. Certain implementations include a rod reduction instrument that is adapted for use with a spinal fixation system and includes a sensor configured to detect a load exerted by a rod reducer on a spinal rod, along with a reduction feedback system that provides an indicator of the load exerted by the rod reducer on the spinal rod.

In particular aspects, a rod reduction instrument adapted for use with a spinal fixation system includes: a rod reducer having a proximal end and a distal end, where the distal end of the rod reducer is configured to engage a spinal rod for seating the spinal rod into a pedicle screw receiver; a sensor configured to detect a load exerted by the rod reducer on the spinal rod during seating of the spinal rod in the pedicle screw receiver; and a reduction feedback system coupled with the sensor, the reduction feedback system configured to: receive load data indicating the load exerted by the rod reducer on the spinal rod from the sensor; and provide an indicator of the load data that is detectable by an operator of the rod reduction instrument.

In additional particular aspects, a method includes providing feedback to an operator during a spinal fixation procedure, the spinal fixation procedure including engaging a spinal rod with a rod reducer to seat the spinal rod into a pedicle screw receiver. The method can further include: receiving, from a sensor, load data indicating a load exerted by the rod reducer on the spinal rod during seating of the spinal rod in the pedicle screw receiver; and providing an indicator of the load data that is detectable by the operator during the spinal fixation procedure.

In further particular aspects, a spinal fixation monitoring system for use in a spinal fixation procedure includes: a plurality of rod reduction instruments adapted for use with a spinal fixation system, each of the rod reduction instruments including: a rod reducer having a proximal end and a distal end, wherein the distal end of the rod reducer is configured to engage a spinal rod for seating the spinal rod into a corresponding pedicle screw receiver; and a sensor configured to detect a load exerted by the rod reducer on a portion of the spinal rod during seating of the spinal rod in the pedicle screw receiver; and a reduction feedback system coupled with the sensor of each of the rod reduction instruments, the reduction feedback system configured to: receive load data indicating the load exerted by each rod reducer on the portion of the spinal rod from a corresponding one of the sensors; and provide an indicator of the load data for at least one of the rod reducers in the plurality of rod reduction instruments, the indicator being detectable by an operator of the plurality of rod reduction instruments.

In other particular aspects, a spinal fixation system includes: a first bone anchor including a first pedicle screw and a receiver; a rod configured to be seated within the receiver of the first bone anchor; an instrument configured to couple to the first bone anchor; and a sensor coupled to the instrument and configured to determine data relating to at least one of: the first bone anchor, the rod or the instrument.

In further particular aspects, a spinal fixation system includes: a first bone anchor including a first pedicle screw and a receiver; a rod configured to be seated within the receiver of the first bone anchor; an instrument configured to couple to the first bone anchor, the instrument having a multi-section shaft; and a sensor mounted axially between distinct sections of the multi-section shaft and configured to determine data relating to at least one of: the first bone anchor, the rod or the instrument.

In other particular aspects, a spinal fixation monitoring system for use in a spinal fixation procedure includes: a plurality of rod reduction instruments adapted for use with a spinal fixation system, each of the rod reduction instruments including: a rod reducer having a proximal end and a distal end, wherein the distal end of the rod reducer is configured to engage a spinal rod for seating the spinal rod into a corresponding pedicle screw receiver; and a sensor configured to detect a load exerted by the rod reducer on a portion of the spinal rod during seating of the spinal rod in the pedicle screw receiver; and a reduction feedback system coupled with the sensor of each of the rod reduction instruments, the reduction feedback system configured to: receive load data indicating the load exerted by each rod reducer on the portion of the spinal rod from a corresponding one of the sensors; provide an indicator of relative loading of a first rod reducer as compared with at least one additional rod reducer in the plurality of rod reduction instruments, and update the indicator of relative loading over time as load data for at least one of the first rod reducer or the additional rod reducers in the plurality of rod reduction instruments is updated.

Implementations may include one of the following features, or any combination thereof.

In certain examples, the rod reduction instrument further includes a housing mounted to the proximal end of the rod reducer, where the reduction feedback system is disposed within the housing.

In some cases, the housing is: a) modular and/or disposable, b) mounted to the existing nut and is disposable, or c) mounted to any portion of the rod reducer.

In particular implementations, the reduction feedback system includes a processor and memory, the memory storing instructions which when executed, cause the processor to: compare the load data with a load threshold for the rod reducer; and provide an indicator that the load data satisfies or does not satisfy the load threshold for the rod reducer.

In certain aspects, the load data at least partially represents an amount of torque applied to a lock screw during tightening of the lock screw within the pedicle screw receiver and a compressive force applied to the rod reducer, wherein the indicator that the load data satisfies or does not satisfy the load threshold includes an indicator of an amount that the compressive force applied to the spinal rod should be modified to satisfy the load threshold for the rod reducer, where the load threshold is based at least in part on a model that correlates clinical data representing patient-specific bone quality with screw pullout.

In certain cases, the load threshold defines a maximum acceptable load exerted by the rod reducer on the spinal rod during seating of the spinal rod in the pedicle screw receiver, wherein the maximum acceptable load is: a) approximately 50 pounds to approximately 250 pounds, b) approximately 25 pounds to approximately 150 pounds, or c) approximately 25 pounds to approximately 75 pounds.

In some aspects, the processor is further configured to: compare the load data with additional load data detected by a set of additional sensors coupled with additional rod reducers; and provide an indicator of relative loading of the rod reducer as compared with at least one of the additional rod reducers in the set.

In particular implementations, the indicator of relative loading indicates whether the rod reducer is more loaded, less loaded or equally loaded relative to the additional rod reducers in the set.

In some cases, the indicator of relative loading always includes an indicator of a least loaded rod reducer in the set.

In certain aspects, the processor is configured to update the indicator of relative loading over time as load data for at least one of the rod reducer or the additional rod reducers in the set is updated.

In particular cases, the reduction instrument is configured for use in a multi-level reduction procedure such that the indicator of the load data comprises an indicator of relative loading of the rod reducer as compared with a set of additional rod reducers engaged with the spinal rod.

In certain implementations, the spinal fixation system includes a set of rod reduction instruments having a set of rod reducers engaged with the spinal rod, and the reduction feedback system is communicatively coupled to each of the rod reduction instruments and is configured to receive load data indicating a load exerted by each rod reducer on the spinal rod.

In some aspects, the set of rod reducers includes up to twenty (20) total rod reducers, arranged in subsets of ten (10) on each side of the patient's spine.

In particular cases, the reduction feedback system is further configured to provide an indicator of reduction order for the set of rod reduction instruments based on the received load data.

In certain aspects, the indicator of reduction order includes instructions for multi-step reduction of the set of rod reduction instruments.

In some implementations, the reduction feedback system is further configured to: compare the load data from two or more of the rod reduction instruments in the set with a set of load thresholds; and provide an indicator prioritizing increased loading of a particular rod reduction instrument over at least one additional rod reduction instrument based on whether the load data from the two or more rod reduction instruments satisfies the set of load thresholds.

In certain cases, the set of load thresholds include absolute loading thresholds for each of the two or more rod reduction instruments.

In particular aspects, absolute loading thresholds vary based on at least one of: a) the location of a given rod reduction instrument along the patient's spine, b) the patient's anatomy, or c) the patient's bone quality.

In some implementations, the set of load thresholds include relative loading thresholds for each of the two or more rod reduction instruments.

In certain aspects, the reduction feedback system includes an electronics compartment physically coupled with the rod reducer, the electronics compartment having at least one of a visual indication system or a tactile indication system for providing the indicator of the load data proximate to the rod reducer.

In particular implementations, the tactile indication system include at least one vibro-tactile actuator.

In some cases, the reduction feedback system further includes a controller coupled with the electronics compartment and coupled with a set of additional electronics compartments on a set of additional rod reduction instruments in the spinal fixation system, where the controller is configured to communicate with the electronics compartment and the set of additional electronics compartments either wirelessly or via a hard-wired connection.

In particular aspects, the hard-wired connection comprises a fiber optic connection.

In certain cases, the visual indication system includes a set of lights configured to be illuminated in at least two distinct patterns to indicate distinctions in the load data, or a display configured to provide at least two distinct visual indicators of the load data.

In some implementations, the display includes a liquid-crystal display (LCD).

In particular aspects, the rod reduction instrument further includes a power source housed in the electronics compartment and coupled with the visual indication system or the tactile indication system.

In certain implementations, the sensor is located between the proximal end and the distal end of the rod reducer.

In some cases, the rod reducer includes a multi-section shaft, and the sensor is mounted axially between distinct sections of the multi-section shaft.

In particular implementations, the sensor is coupled to the proximal end of the rod reducer.

In certain aspects, the sensor is located in a housing with at least a portion of the reduction feedback system.

In some cases, the sensor includes at least one of: a strain gauge, pressure-sensitive film, or a capacitive sensor.

In particular implementations, the rod reduction instrument further includes a guide assembly configured to couple with the pedicle screw receiver and receive the rod reducer therein.

In certain cases, the rod reducer is configured to fully seat the spinal rod into the pedicle screw receiver and enable the spinal rod to be secured to the pedicle screw receiver.

In some aspects, the reduction feedback system is located at the rod reducer or at an output device separate from the rod reducer.

In particular implementations, the output device includes at least one of: a) a user interface, b) a display, c) an audio system, or d) a surgical procedure interface.

In certain cases, in the spinal fixation system, the rod reducer sits within a guide assembly that couples with the pedicle screw receiver, where the rod reducer is configured to fully seat the spinal rod into the pedicle screw receiver and enable the spinal rod to be secured to the pedicle screw receiver.

In particular aspects, the reduction feedback system includes a housing mounted to the proximal end of each of the rod reducers for providing the indicator of the load data proximate to each of the rod reducers.

In certain cases, the sensor that is coupled to the instrument and is configured to determine data relating to at least one of: the first bone anchor, the rod or the instrument, determines data including load data.

In some implementations, the instrument configured to couple to the first bone anchor is a reduction instrument configured to seat the rod within the receiver, and the load data includes a load exerted by the reduction instrument on the rod during seating of the rod into the receiver of the first bone anchor.

In particular aspects, the sensor that is coupled to the instrument is configured to determine data relating to at least one of: the first bone anchor, the rod or the instrument, and determines data including a tensile load between the rod and the bone anchor when the rod is at least partially seated within the bone anchor.

In some cases, the sensor that is coupled to the instrument is configured to determine data relating to at least one of: the first bone anchor, the rod or the instrument, and determines data including torsional force data. In particular aspects, the instrument is a driver configured to tighten a lock screw within the receiver and lock the rod relative to the bone anchor, and the torsional force data includes a torsional force on the lock screw during tightening of the lock screw within the receiver. In additional particular aspects, the instrument is a driver configured to seat the rod within the receiver and tighten a lock screw within the receiver to thereby lock the rod relative to the bone anchor, and the torsional force data includes a torsional force on the lock screw during tightening of the lock screw within the receiver.

In certain cases, the instrument configured to couple to the first bone anchor includes: a rod reduction instrument configured to seat the rod within the receiver; and a driver configured to be inserted through the rod reduction instrument to deliver and tighten a lock screw within the receiver to lock the rod relative to the bone anchor. In some of these aspects, the data includes at least one of: a load exerted by the reduction instrument on the rod during seating of the rod into the receiver of the first bone anchor, or a tensile load between the rod and the bone anchor when the rod is at least partially seated within the bone anchor. In some additional aspects, the data includes a torsional force on the lock screw during tightening of the lock screw within the receiver.

In particular implementations, the spinal fixation system further includes a navigation system communicatively coupled with the instrument and configured to detect a position of the instrument. In certain of these cases, the navigation system is configured to determine a distance moved by the instrument when the instrument changes position, and the navigation system communicates the distance to a processor.

Two or more features described in this disclosure, including those described in this summary section, may be combined to form implementations not specifically described herein.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

The details of one or more implementations are set forth in the accompanying drawings and the description below. Other features, objects and benefits will be apparent from the description and drawings, and from the claims.

Figures 1, 2:
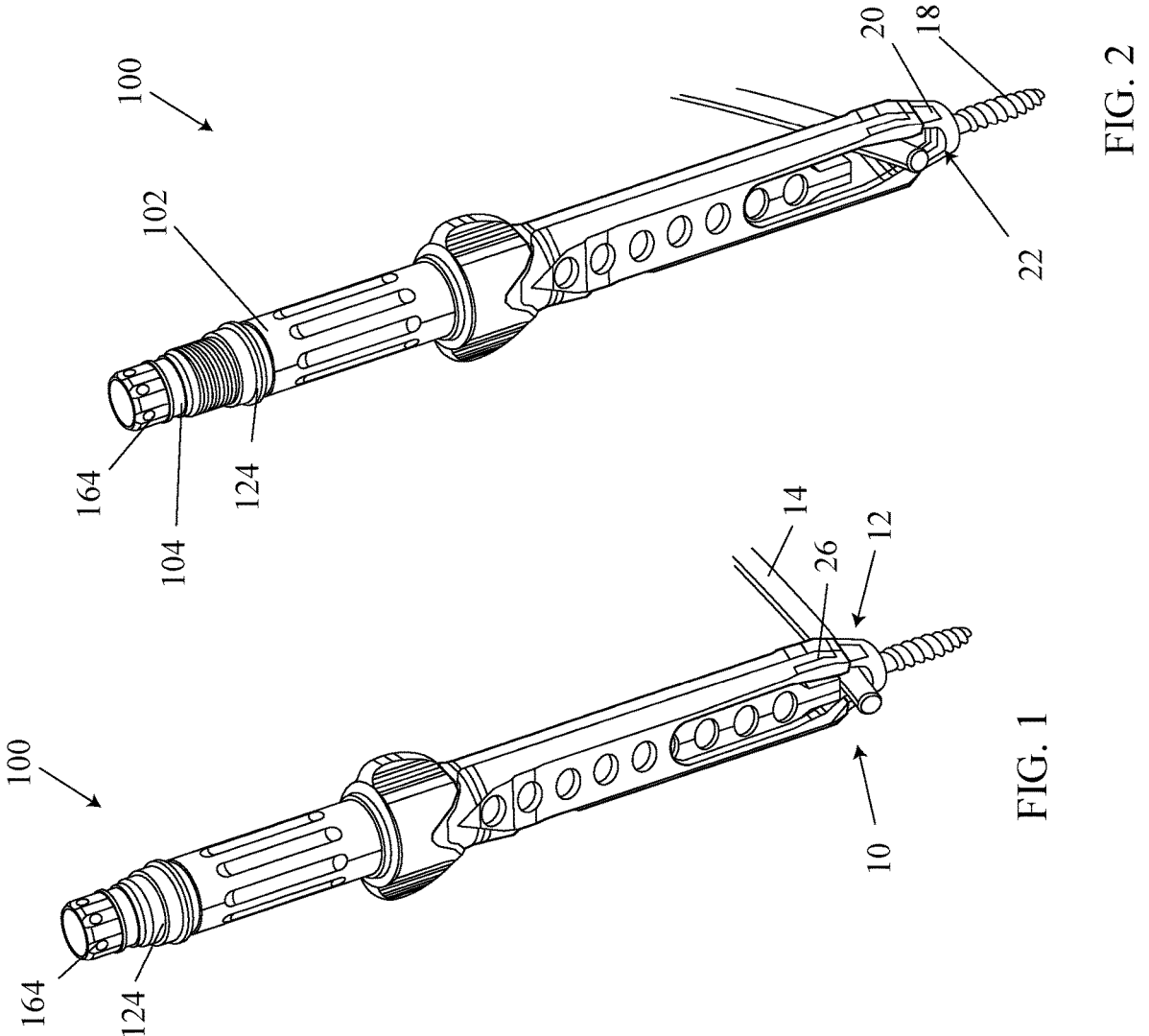
FIG. 1 shows a perspective view of a rod reducer according to various implementations.
FIG. 2 shows an additional perspective view of a rod reducer according to various implementations.
Figures 3, 4, 5, 6:
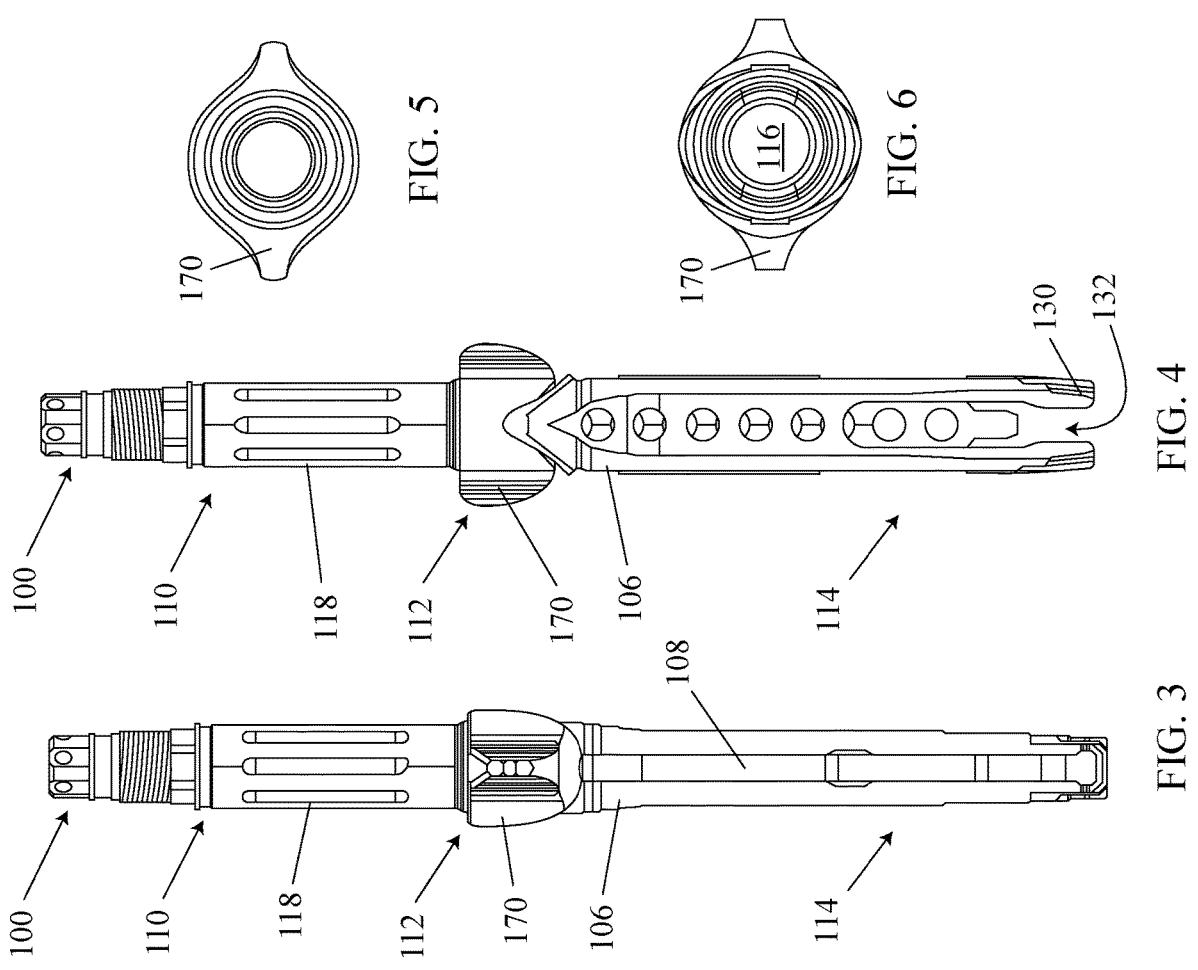
FIG. 3 and FIG. 4 show distinct side views, respectively, of a rod reducer according to various implementations.
FIG. 5 and FIG. 6 show top and bottom views, respectively, of a sleeve for the rod reducer of FIGS. 3 and 4.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

Various example embodiments of devices and techniques for rod reduction during spinal instrumentation procedures are described herein. In the interest of clarity, not all features of an actual implementation are necessarily described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The rod reduction instruments and related systems, program products and methods described herein boast a variety of inventive features and components that warrant patent protection, both individually and in combination.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

This disclosure provides, at least in part, a rod reduction instrument, related fixation systems, methods and monitoring systems that beneficially incorporate a reduction feedback system to enhance efficacy of spinal fixation procedures, as well as mitigate opportunity for operator (e.g., surgeon) error in performing such procedures. The various disclosed implementations can improve patient outcomes when compared with conventional spinal fixation procedures. The disclosed implementations can provide real-time and/or post-operative feedback on reduction procedures, enhancing both current procedural outcomes as well as future surgical outcomes. In particular cases, the reduction feedback system can provide information to an operator regarding desired reduction ordering in a multi-level reduction procedure, thereby mitigating or avoiding overloading of instruments at any given time during the procedure.

Commonly labeled components in the FIGURES are considered to be substantially equivalent components for the purposes of illustration, and redundant discussion of those components is omitted for clarity.

FIGS. 1 and 2 illustrate perspective views of example rod reduction instruments, or reducers, according to various implementations. It is understood that the disclosed implementations can be applied to a number of rod reduction instruments in various form factors. For example, additional rod reduction instruments such as those disclosed in U.S. Pat. No. 10,136,927 (entirely incorporated by reference herein) can benefit from the various disclosed implementations. In various implementations, the example rod reduction instruments (reducers) are used during the installation of a fixation construct 10 onto the spine of a patient. The fixation construct 10 includes anchor members 12 connected by a fixation rod 14 locked to each anchor 12. An anchor 12 is implanted in each vertebra to be fixed by the construct 10. For example, two anchors 12 may be used to fix two vertebrae together; three may be used to fix three vertebrae together; four may be used to fix four vertebrae together; and so on. Additionally, multiple anchors 12 may be used to fix each vertebrae to adjacent vertebrae (e.g., four anchors 12 can be used to couple two vertebrae together). The anchor 12 includes a bone anchor 18 and a housing 20 for capturing and locking a fixation rod 14. The bone anchor 18 may be a bone screw suitable for stable fixation to vertebral bone (e.g. pedicle or vertebral body), as shown. The bone anchor 18 may also include other fixation devices (e.g. hooks, staples, clamps, etc. . . . ). The housing 20 has a base that attaches with the bone anchor and a pair of upstanding arms that together form a rod channel 22. The housing also includes a mechanism to lock the fixation rod 14 in position in the rod channel 22. For example, the mechanism may include a locking cap guide and advancement feature disposed on the interior face of each arm that interacts with a complementary feature on a locking cap. The base may be fixed to the anchor 18 or may be coupled such that the housing 20 can rotate in one or more directions (e.g. polyaxial). The housing 20 also includes one or more instrument engagement features for releasably coupling to one or more instruments during implantation. Example of anchors configured for use with the reducers described herein are shown and described in U.S. Pat. No. 9,198,698 ("Minimally Invasive Spinal Fixation System and Related Methods") and U.S. Pat. No. 11,051,861 ("Rod Reduction Assemblies and Related Methods"), the entire contents of each of which are incorporated herein by reference. The reducers described herein can be engaged to one or more of the anchors 12 of the fixation construct 10 to facilitate alignment and advancement of the rod 14 into the rod channel 22 of each anchor. In particular implementations, the fixation construct 10 includes a pedicle screw.

Now with reference to FIGS. 1-6, a rod reducer (or simply, reducer) 100 according to one example embodiment is illustrated. The reducer 100 is configured to couple to both arms of anchor 12 and impart a downward force on the rod 14. The downward force on the rod acts to draw the rod 14 and anchor housing 20 together until the rod 14 fully seats in the rod channel 22. A locking mechanism, such as locking cap may then be at least partially engaged to capture the rod 14 in the housing 20 prior to decoupling the reducer 100 from the anchor 12. The reducer 100 includes a coupling unit 102 (FIG. 2) that connects to the anchor 12 and a translation unit 104 (FIG. 2) that translates relative to the coupling unit 102 to urge the rod 14 towards the anchor.

The coupling unit 102 includes a base member 106 and first and second attachment arms 108 that are pivotally coupled with the base member 106. The base member 106 is an elongated, generally tubular member having a proximal portion 110, a central portion 112, a distal portion 114, and a central lumen 116 (FIG. 6) extending longitudinally through the entire length of the base member 106. The proximal portion 110 includes a handle 118 that provides a gripping area for a user to grip the reducer 100. Above the handle 118 is a head 124 (FIGS. 1-2) that allows the coupling of other instruments with the reducer 100. The head 124 may be configured to mimic the proximal end of minimally invasive screw guides such that any instruments that engage or couple with the guides may also engage or couple with the reducer 100 (for example, vertebral body derotation assemblies, counter torques, etc. . . . ). Not shown, the proximal portion 110 can include a threaded portion formed on the interior of the proximal portion 110 (i.e. the proximal end of the lumen 116) for threadedly engaging the translating unit 104. In certain implementations, a drive knob 170 is located between the proximal portion 110 and the central portion 112.

Figure 7:
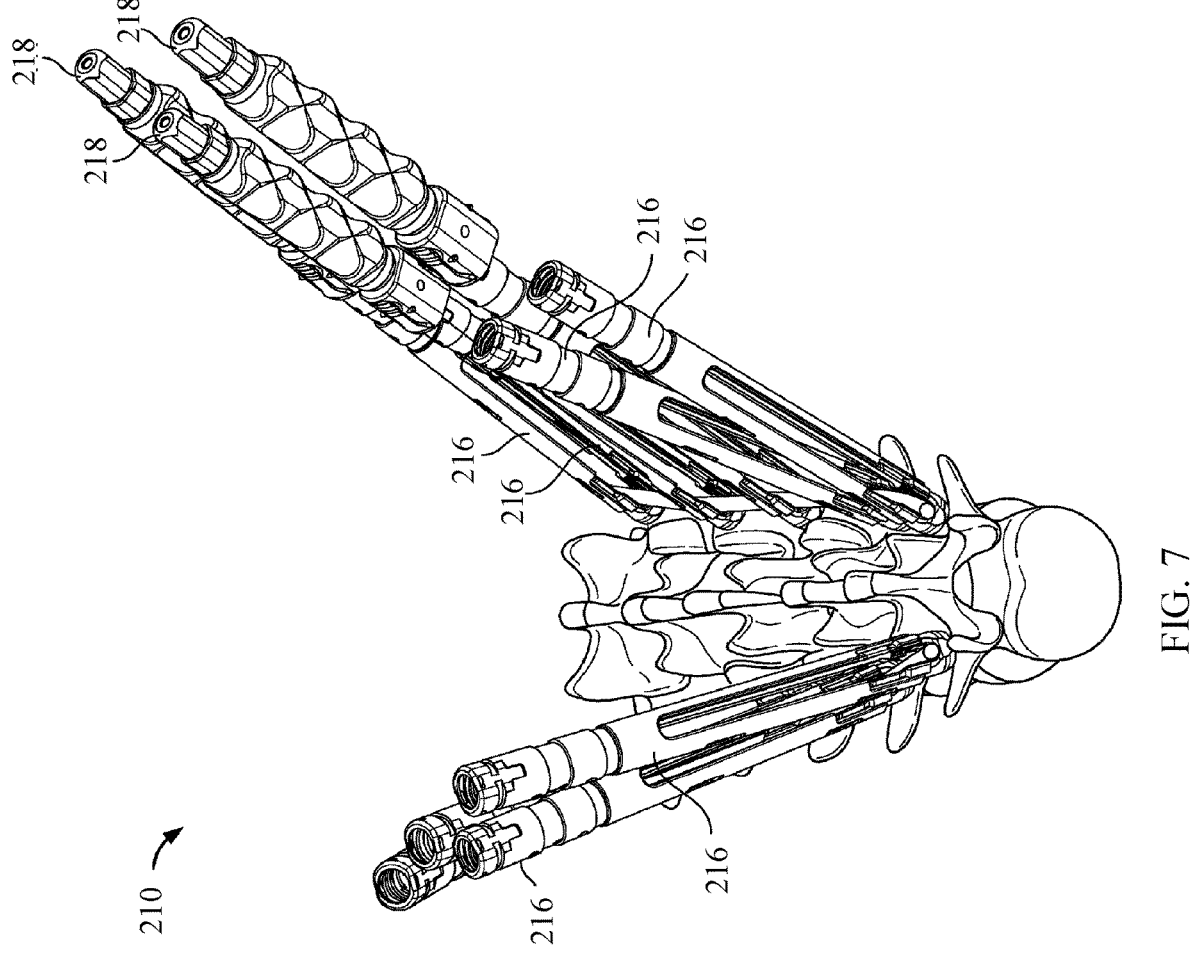
FIG. 7 shows a perspective view of a spinal fixation system according to various implementations.
Figure 8:
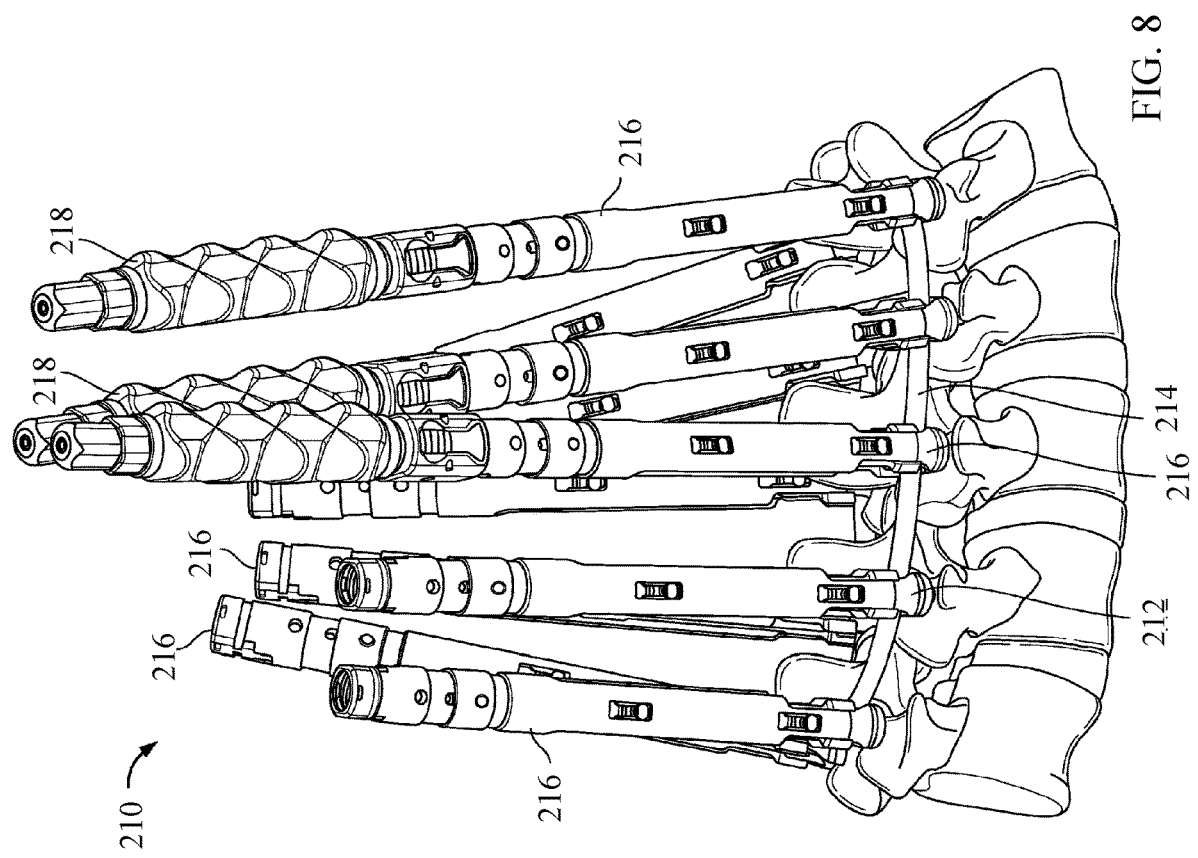
FIG. 8 shows a distinct perspective view of the spinal fixation system of FIG. 7, according to various implementations.

FIGS. 7 and 8 illustrate a spinal fixation system 210 configured for introducing and building a posterior spinal fixation construct such as that described above, according to one example embodiment. According to one example, the spinal fixation system 210 includes a pedicle screw 212, an elongated spinal rod 214, and a guide assembly 216. Pedicle screws 212 are inserted bilaterally or unilaterally into multiple vertebra across one or more levels. In additional implementations, a fixation anchor (such as those described in U.S. Pat. No. 9,198,698, previously incorporated by reference herein) can be utilized in place of pedicle screw 212 in one or more vertebra. The spinal fixation system 210 may further include any of a variety of instruments configured to perform the installation and assembly of the spinal fixation construct, including by way of example a reduction instrument (also called a reducer) 218 shown in FIGS. 7 and 8, as well as rod inserters, compression instruments, lock screw inserters, guide adjusters, tap guides, and dilators, of which various embodiments are described in further detail in U.S. Pat. No. 9,198,698, previously incorporated by reference herein.

Figure 9:
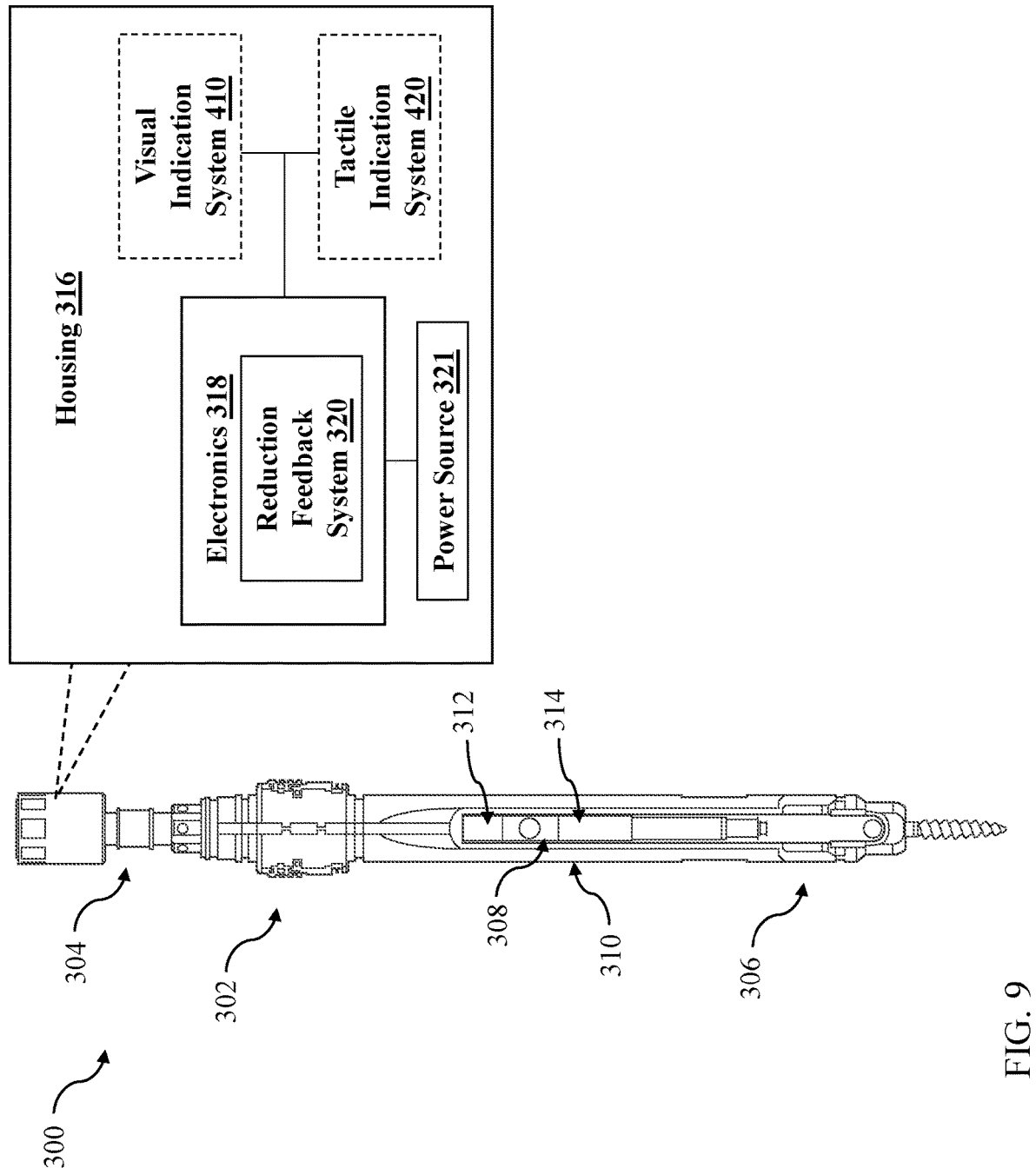
FIG. 9 is a schematic side view of a rod reducer and associated electronics according to various implementations.

FIG. 9 shows an example implementation of a rod reduction instrument (or simply, instrument) 300 according to various implementations. As illustrated in FIG. 9, the instrument 300 includes a rod reducer (or simply, reducer) 302, which can be similar in form and/or function to the reducer(s) described according to any implementation herein, e.g., reducer 100 and/or reducer 218. In particular implementations, the reducer 302 has a proximal end 304 and a distal end 306. The distal end 306 is configured to engage a spinal rod for seating the spinal rod into a pedicle screw receiver (e.g., as described with respect to FIGS. 1-4). In various implementations, the rod reducer 302 is configured to fully seat the spinal rod (e.g., spinal rod 214 in FIG. 8) into the pedicle screw receiver (e.g., the receiver of the pedicle screw 212 in FIG. 8, also referred to as the rod channel 22 in FIG. 2).

In particular implementations, the instrument 300 includes a sensor 308 configured to detect a load exerted by the rod reducer 302 on the spinal rod during seating of the spinal rod in the pedicle screw receiver. In particular examples, the sensor 308 includes one or more of: a strain gauge, a pressure-sensitive film, or a capacitive sensor. In various implementations, the sensor 308 is configured to sense a load applied via the rod reducer 302, e.g., on the spinal rod. In certain examples, the sensor 308 is configured to indicate a pressure and/or torque applied by the rod reducer 302, e.g., on the spinal rod.

In certain implementations, the sensor 308 is configured to determine data relating to at least one of: a bone anchor (e.g., anchor 12 in FIGS. 1-6 and/or pedicle screw 212 in FIGS. 7 and 8), a spinal rod (e.g., rod 14 in FIGS. 1-6 and/or spinal rod 214 in FIGS. 7 and 8), or the reducer 302. In certain examples, the sensor 308 provides load data including a tensile load between the rod and the bone anchor when the rod is at least partially seated within the bone anchor. In additional examples, the sensor 308 provides load data including torsional force data.

Figure 10:
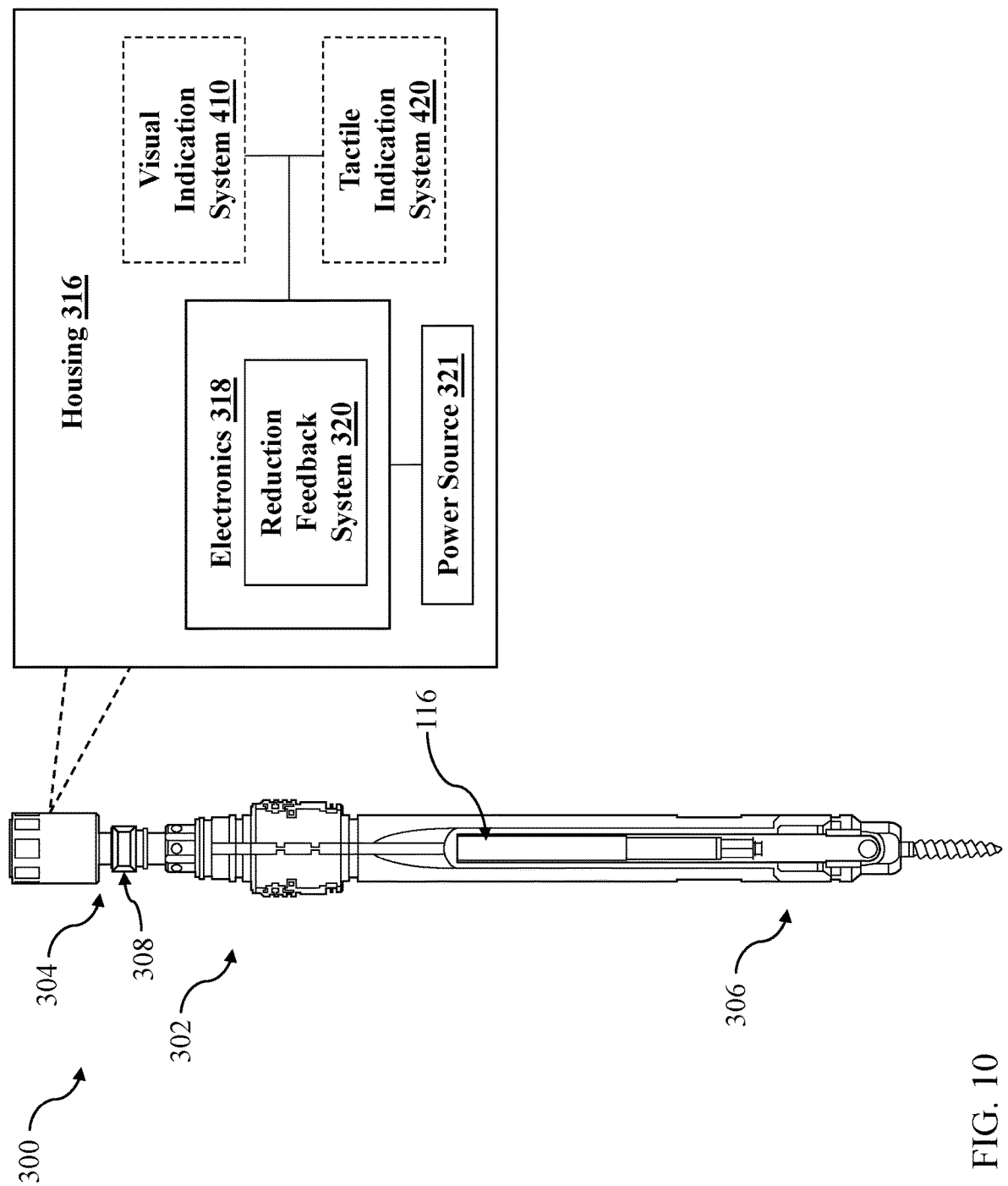
FIG. 10 is a schematic side view of a rod reducer and associated electronics according to various additional implementations.

In particular implementations, the sensor 308 is located between the proximal end 304 and the distal end 306 of the rod reducer 302. For example, as illustrated in FIG. 9, the reducer 302 includes a multi-section shaft 310, including a first section 312 and a second section 314, and the sensor 308 is mounted axially between the sections 312, 314. In additional examples, such as illustrated in FIG. 10, the sensor 308 is coupled to the proximal end 304 of the rod reducer 302, e.g., on an end of the rod reducer 302.

In particular implementations, a housing 316 is coupled to the reducer 302, e.g., at the proximal end 304 of the reducer 302. In certain cases, the housing 316 includes electronics 318 as described herein. In additional implementations, the electronics 318 are configured to communicate (e.g., wirelessly and/or hard-wired connection) with a remote spinal fixation management system. In particular cases, the electronics 318 include at least one portion of a reduction feedback system 320.

The sensor 308 is coupled with the reduction feedback system 320 that is configured to: a) receive load data indicating the load exerted by the rod reducer 302 on the spinal rod from the sensor; and b) provide an indicator of the load data such that the indicator is detectable by an operator of the instrument 300. As described herein and indicated in phantom in FIG. 9, the reduction feedback system 320 can be at least partially disposed in the housing 316 mounted to the proximal end 304 of the reducer 302. In additional implementations, the reduction feedback system 320 is at least partially located in a centralized spinal fixation management system, described further herein.

In certain cases, the housing 316 is modular and/or disposable. That is, in certain cases, the housing 316 substantially contains the reduction feedback system 320 and is able to be selectively coupled and/or decoupled with the proximal end 304 of the reducer (e.g., with selective couplers such as male/female threading, snap-fit connectors, pressure or force-fit connectors, adhesive(s), etc.). In certain of these cases, the reduction feedback system 320 is disposable, that is, intended for one-time use during a spinal fixation procedure. In these examples, the reduction feedback system 320 can include onboard electronics that are intended for limited usage, e.g., sensor(s) 308, power, and signal conditioning electronics such as an interface circuit to process and output a signal. In certain cases, the interface circuit includes a signal processor such as a digital signal processor (DSP), a logic engine to filter/condition the signal, and a controller to control onboard functions such as displays and transmission of signals to external components such as an external receiver. In particular examples, the housing 316 is selectively coupled to an existing nut on the proximal end 304 of the reducer 302. In additional examples, the housing 316 is selectively coupled to the central lumen 116 or another portion of the body of the reducer 302.

Figure 11:
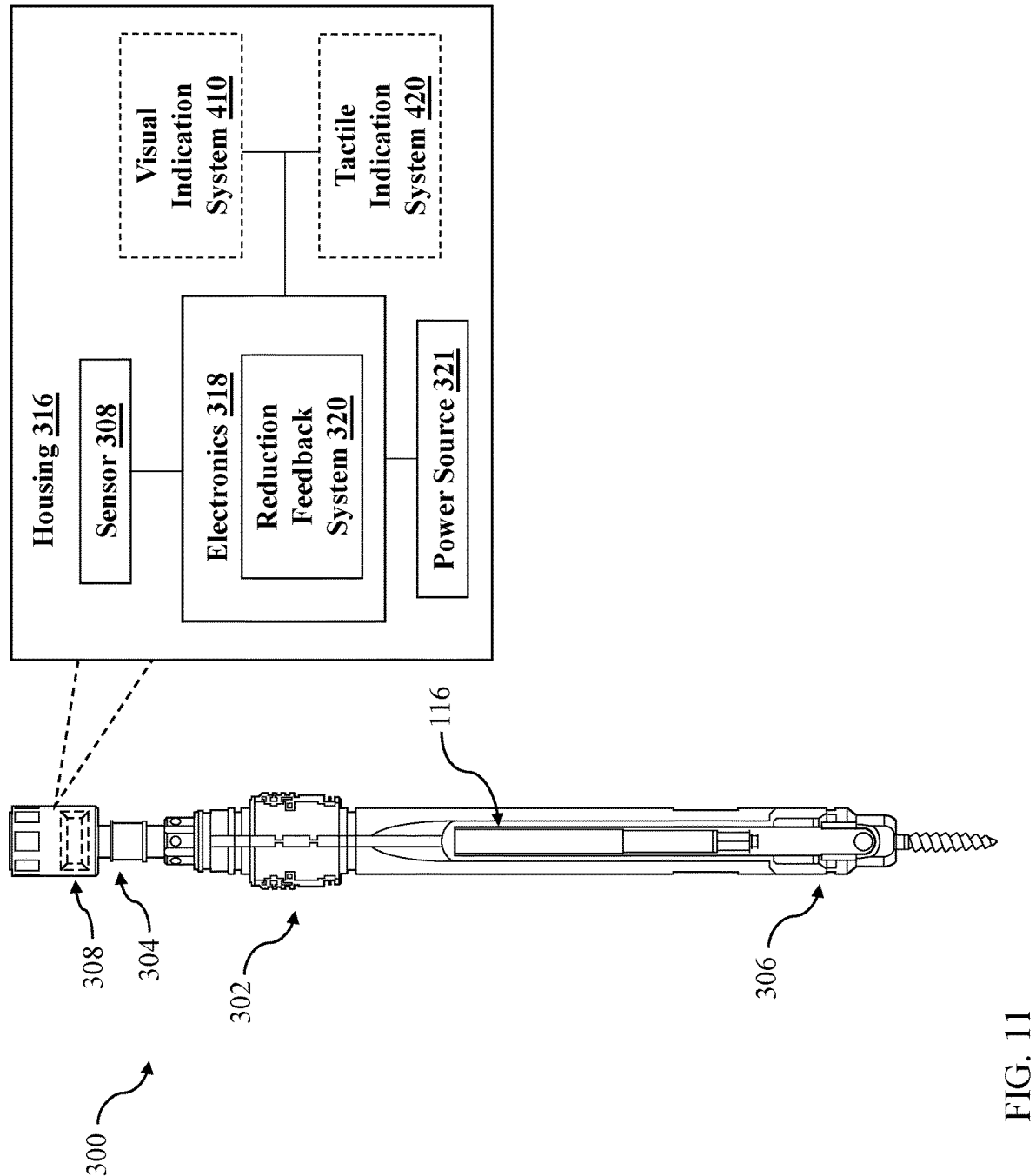
FIG. 11 is a schematic side view of a rod reducer and associated electronics according to various further implementations.

In certain examples, as illustrated in FIG. 11, the sensor 308 is located within the housing 316 with at least a portion of the reduction feedback system 320. In these implementations, the sensor 308 can be directly coupled with the reduction feedback system 320, or at least the portion of the reduction feedback system 320 that is present in the housing 316. In particular cases, the electronics 318 are powered by an onboard power source 321 at the housing 316 (e.g., one or more batteries, charging devices and/or hard-wired power sources).

Figure 12:
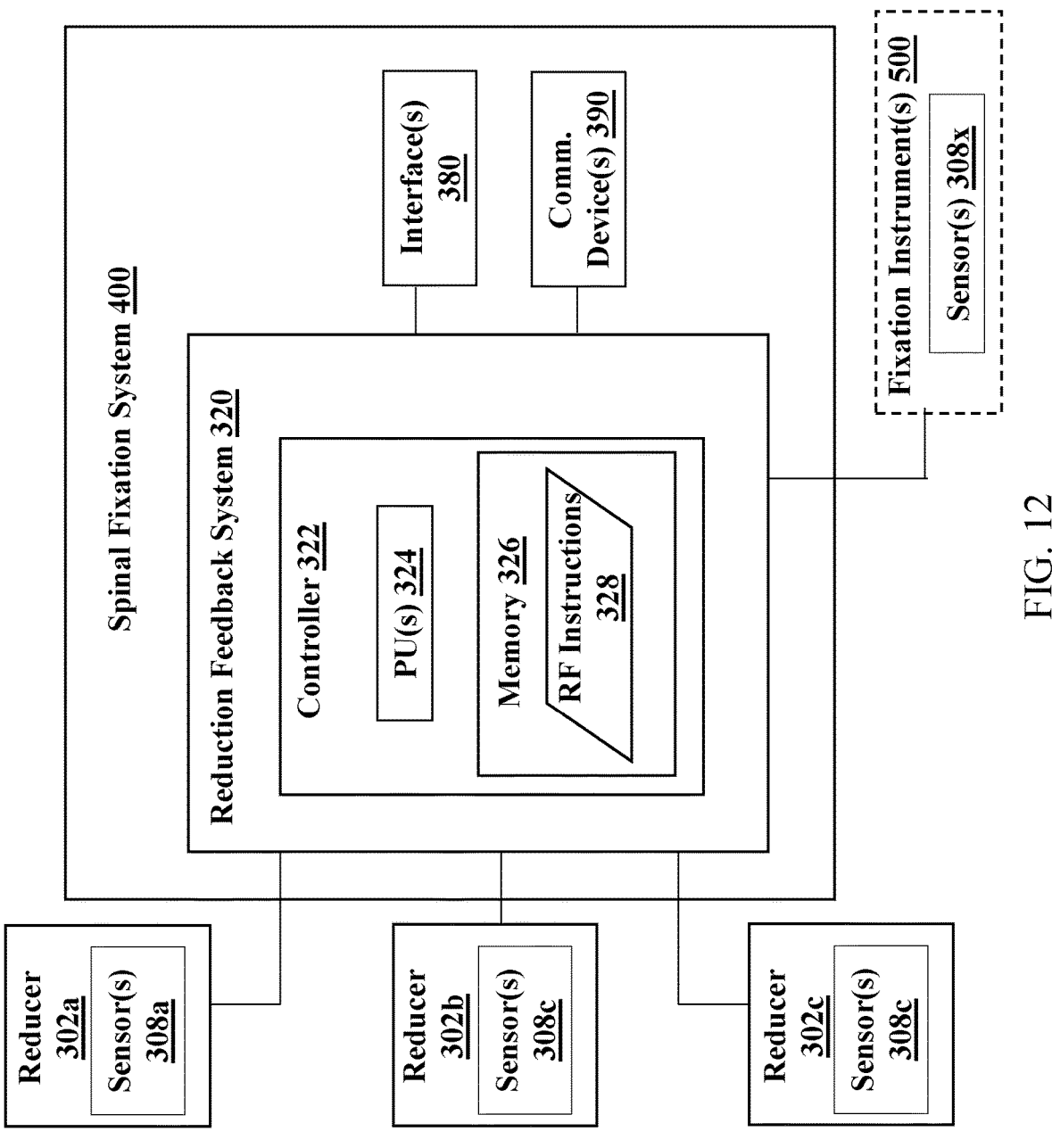
FIG. 12 is a system diagram illustrating a spinal fixation system and instruments according to various implementations.

A schematic depiction of the reduction feedback system 320, including data flows related to components that interact with the system 320, is illustrated in FIG. 12. As described herein, the reduction feedback system 320 can function as an onboard (e.g., on instrument 300) system and/or a physically separate system (e.g., coupled via a wireless and/or hard wired connection). In certain cases, as described herein, the reduction feedback system 320 is hosted, or otherwise executed as part of a spinal fixation system 400, for example, as described in U.S. patent application Ser. No. 16/562,411 (Systems and Methods for Spinal Surgical Procedures), herein incorporated by reference in its entirety.

In particular implementations, the reduction feedback system 320 includes a controller 322 (e.g., one or more microcontrollers), that includes at least one processor (PU) 324 (such as one or more microprocessors) and is coupled with or contains a memory 326 (e.g., including one or more storage components such as memory chips and/or chipsets). The memory 326 stores instructions (e.g., reduction feedback (RF) instructions 328) which when executed by the PU(s) 324 cause the PU 324 to: i) compare the load data obtained from the sensor 308 with a load threshold for the reducer 302; and ii) provide an indicator that the load data satisfies or does not satisfy the load threshold for the reducer 302. In particular cases, the load threshold includes a load range for the reducer 302 that is indicative of a desired loading of the anchor (e.g., anchor 12, FIG. 1, or pedicle screw 212, FIGS. 7, 8). In various implementations, the load threshold includes a range with an upper and lower bound, which can account for some variation in measurement based on a known measurement margin of error, e.g., of the sensor 308. In additional implementations, the load threshold includes a load value that accounts for a known measurement error, e.g., by one, two, or three percent. In certain implementations, the load threshold is based at least in part on a model that correlates clinical data representing patient-specific bone quality with screw pullout. This clinical data can be engrained in a model stored in the reduction feedback instructions 328, and can be updatable, e.g., as further data becomes available.

In particular implementations, the load data at least partially represents an amount of torque applied to a lock screw during tightening of the lock screw within the pedicle screw receiver (FIG. 8) and a compressive force applied to the reducer 302. In certain of these cases, e.g., where the load data does not satisfy the load threshold, the indicator can include an indicator of an amount that the torque applied to the spinal rod should be modified to satisfy the load threshold for the reducer 302.

In particular implementations, the load threshold(s) defines a maximum acceptable load exerted by the reducer 302 on the spinal rod 214 (FIG. 8) during seating of the spinal rod in the receiver of the pedicle screw 212 (FIG. 8), also referred to as the rod channel 22 (FIG. 2). In certain cases, the maximum acceptable load is one of: a) approximately 50 pounds to approximately 250 pounds, b) approximately 25 pounds to approximately 150 pounds, or c) approximately 25 pounds to approximately 75 pounds. In certain cases, the maximum acceptable load ranges (a)-(c) are combinable, e.g., approximately 50 pounds to approximately 150 pounds, approximately 25 pounds to approximately 250 pounds, etc.

Figure 14:
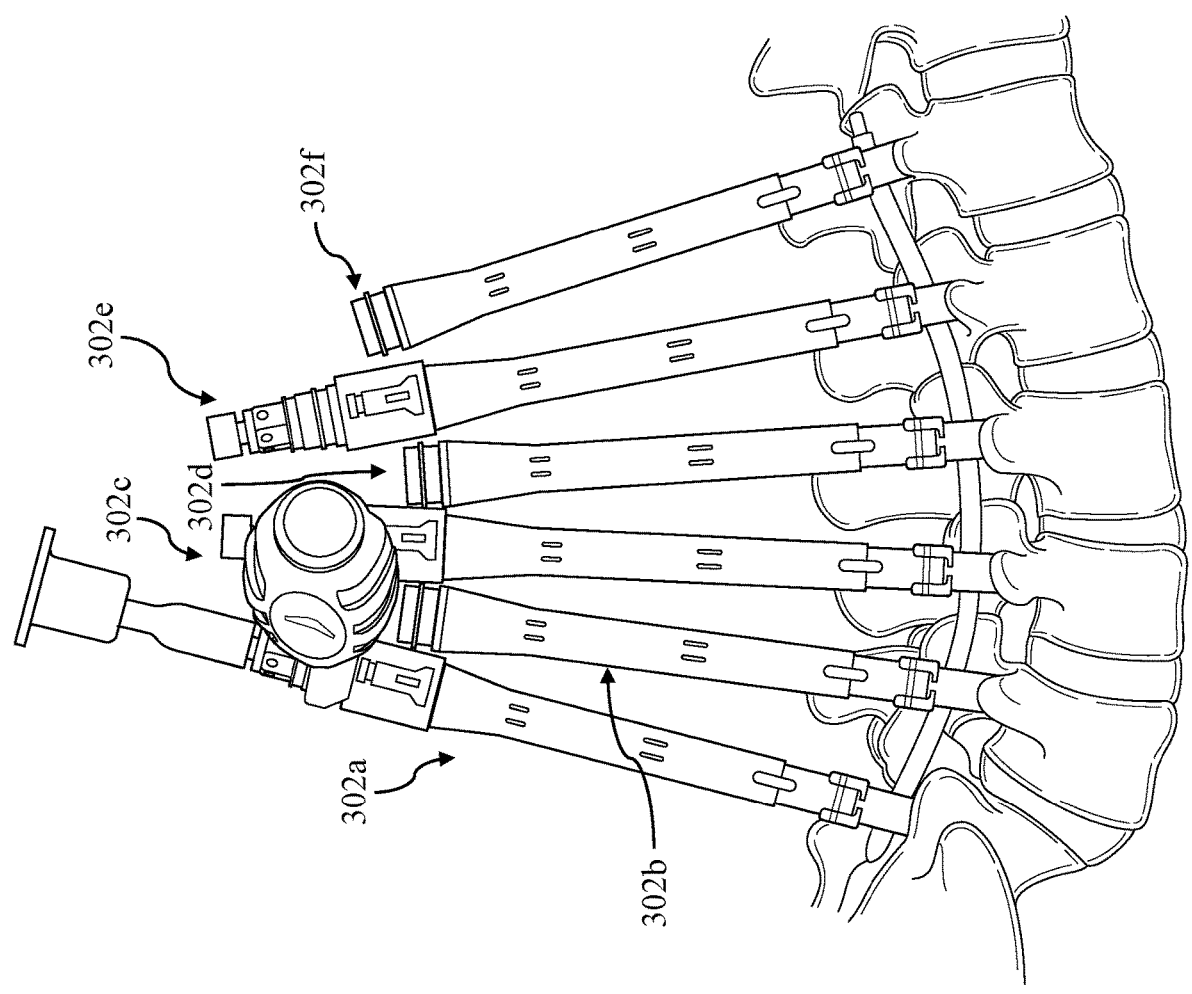
FIG. 14 is a side view of a portion of a spinal fixation system according to various implementations.

With continuing reference to FIG. 12, an example depiction of a reduction feedback system 320 for managing a set of rod reducers 302a, 302b, 302c is illustrated. In these cases, the reduction feedback system 320 can be part of a spinal fixation system 400 that is configured to manage reducers 302 in a multi-level reduction procedure, e.g., where two or more vertebral adjustments are made along a patient's spine. In various implementations, a set of rod reducers 302 are engaged with the spinal rod, and the reduction feedback system 320 is communicatively coupled to each of the rod reduction instruments (e.g., wirelessly or via hard-wired means) and is configured to receive load data indicating a load exerted by each rod reducer 302 on the spinal rod. This depiction includes a few rod reducers 302a, 302b, 302c for simplicity of illustration, but it is understood that the set of rod reducers can include up to twenty (20) total rod reducers, arranged in subsets of ten (10) on each side of the patient's spine. FIG. 14 illustrates an example implementation depicting six reducers 302a-f arranged on one side of a patient's spine, which during an alignment procedure, would correspond with six additional reducers 302 (not shown) on the opposite side of the patient's spine (for a total of twelve (12) reducers 302).

In particular implementations, the reduction feedback system 320 is coupled with sensors 308a, 308b, 308c, etc., either directly (such as via a wireless connection or hard-wired connection), or via the onboard reduction feedback system 320 at each of the reducers 302a, 302b, 302c, etc. In certain cases, the reducers 302 (including sensors 308) are configured to communicate with the reduction feedback system 320 via a communications device, e.g., in electronics 318 and/or at spinal fixation system 400 (FIG. 12). The communications device(s) can include one or more transmitters and/or receivers (e.g., wireless and/or hard-wired transmitters/receivers). In various implementations, the communication devices are configured for a plurality of communication protocols, e.g., wireless protocols such as WiFi, Bluetooth, BLE, Zigbee, etc., as well as radio communication and intercom communications, and/or a hard-wired connection (e.g., fiber optic connection).

Figure 13:
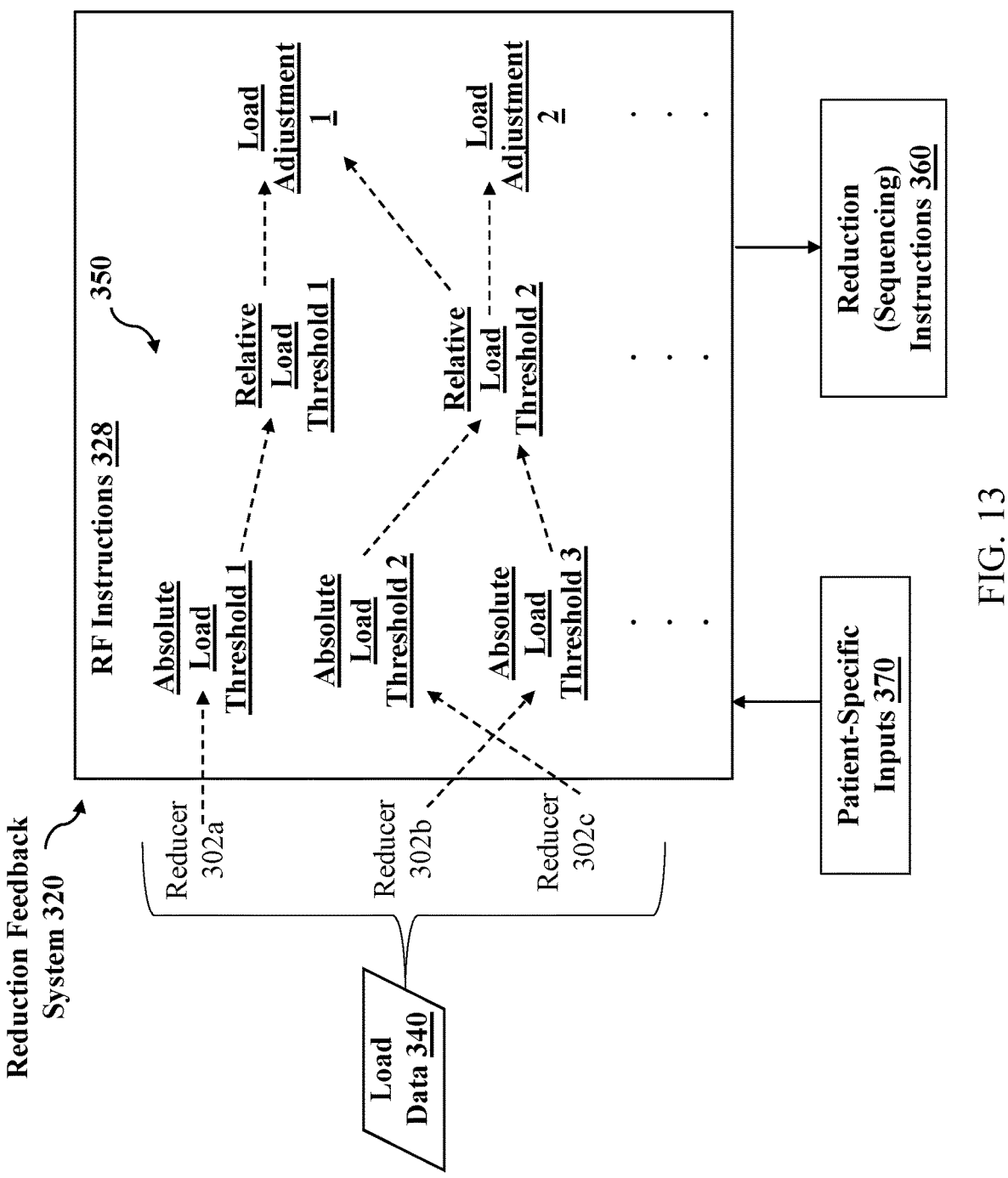
FIG. 13 is an example data flow diagram illustrating reduction ordering according to various implementations.

In any case, the reduction feedback system 320 (and particularly, PU(s) 324) is configured to compare the load data received from one or more sensors 308 with corresponding load thresholds for those sensors 308 in order to determine whether one or more reducers 302 is appropriately loaded (e.g., over or under loaded). FIG. 13 illustrates an example data structure of the RF instructions 328 for comparing load data 340 with a set of thresholds 350 in order to determine: a) whether a particular reducer 302 is under or over loaded, and b) a reduction order for adjusting the load on a plurality of reducers 302. Based on the load data 340, the RF instructions 328 provide reduction (sequencing) instructions 360, such as an identifier of one or more reducers 302 and an amount of load adjustment. In certain cases, the reduction instructions 360 include reduction sequencing instructions, such as where a plurality of load data 340 are obtained as part of a multi-level reduction procedure.

With reference to FIGS. 12-14, in various implementations, the reduction feedback system 320 is configured to compare load data 340 from each of a plurality of sensors 308 and provide reduction instructions 360, which can include an indicator of relative loading between at least two of the reducers 302. For example, the indicator of relative loading can indicate whether a given rod reducer (e.g., reducer 302b) is more loaded, less loaded or equally loaded relative to any one of or all of the additional rod reducers (e.g., reducers 302a, 302c) in the set. In various implementations, load data 340 is continuously, or periodically, updated during the alignment procedure, such that new load data 340 is processed by the reduction feedback system 320 for an extended period during the procedure. In particular cases, load data 340 is updated every time a change in load at one of the sensors 308 is detected, e.g., at every adjustment by the surgeon. In these cases, the reduction instructions 360 are continuously updated to reflect the relative load on each reducer 302 in the set. In example implementations, the indicator of relative loading always includes an indicator of a least loaded rod reducer 302 in the set of reducers, such that the system 320 is configured to update the indicator of relative loading over time as load data for at least one of the reducers 302 in the set is updated.

As illustrated in FIG. 13, the reduction instructions 360 can include an indicator of reduction order (or sequencing) for the set of reducers 302a, 302b, 302c, etc. based on the received load data 340. For example, the indicator of reduction order can include reduction instructions 360 for multi-step reduction of the set of reducers 302. In particular, FIG. 13 illustrates an example implementation where the system 320: i) compares the load data 340 from two or more reduction instruments (e.g., reducers 302) with a set of thresholds 350, and ii) provides an indicator prioritizing modified loading (e.g., increased or decreased loading) of a particular reduction instrument (e.g., reducer 302b) over at least one additional reduction instrument (e.g., reducer 302a) based on whether the load data 340 from the two or more reduction instruments 302a, 302b, satisfies the set of load thresholds. In some cases, the thresholds 350 include absolute loading thresholds (e.g., Absolute Loading Thresholds 1, 2, 3) for each of the reducers 302. These absolute loading thresholds can represent a minimum and/or maximum acceptable load value for the load data 340 (e.g., as detected by sensor(s) 308). In certain cases, absolute loading thresholds vary based on at least one of: a) location of a given rod reduction instrument (e.g., reducer 302) along the patient's spine, b) the patient's anatomy (e.g., curvature of the spine), or c) the patient's bone quality. For example, the RF instructions 328 can be adjusted or otherwise tailored according to patient-specific inputs 370, which can include characteristics of the patient (e.g., physiological and/or anatomical characteristics such as spacing between vertebrae, angulation of one or more sections of the patient's spine, etc.), as well as the patient's bone quality (e.g., on a mechanical bone quality scale such as a T-score (comparing relative health to a standard), or a quality indicator derived from a bone scan such as a CT scan or MRI). For example, absolute loading thresholds can be adjusted based on the patient's bone quality (e.g., lower maximum absolute load threshold for lower bone quality), and/or the angulation of adjacent vertebrae in which the reducers 302 are operating (e.g., higher minimum absolute load threshold for higher angulation value). Additionally, the RF instructions 328 can be adjusted based on the location of a given reducer 302 along the spine, e.g., with distinct absolute loading thresholds at L2 versus L4.

Even further, the load thresholds 350 can include relative loading thresholds (e.g., Relative Load Threshold 1, Relative Load Threshold 2) for each of the two or more rod reduction instruments (e.g., reducers 302a, 302b, 302c, etc.). In these cases, the relative loading thresholds can define a maximum allowable difference in loading between any two reducers 302, and/or between any two adjacent reducers (e.g., between reducers 302a and 302b, or reducers 302d and 302e, FIG. 14). These relative loading thresholds can be used to determine a reduction order, e.g., to prioritize loading a particular reducer 302a over another reducer 302c. In the example shown in FIG. 13, load data 340 is processed using absolute load thresholds prior to relative load thresholds, but this order can be reversed in various implementations. In additional implementations, loading thresholds and relative loads can be used to construct a reduction order, e.g., for instructing a user such as a surgeon or other medical professional. In some cases, the load data 340 for reducer(s) 302 is analyzed based on one or more of: i) a threshold for a given reducer 302 or an aggregate threshold for a group of reducers 302, to avoid exceeding a threshold for reducer(s) 302; ii) relative loading between reducers 302, to avoid a loading difference between any two or more reducers 302 exceeding a difference threshold; iii) an upper and/or lower reduction bound during manipulation of a reducer 302, or iv) to comply with a reduction order prescribed by pre-operation planning. In certain cases, after comparing the load data 340 for two or more reducers 302a, 302b, 302c, etc., the system 320 provides at least one load adjustment (e.g., Load Adjustment 1, Load Adjustment 2, etc.), which is placed in an ordered listing for use as reduction (sequencing) instructions 360. For example, reduction (sequencing) instructions 360 can include Load Adjustment 1 (e.g., adjust torque on reducer 302b with clockwise quarter turn or X lbs of pressure increase), followed by Load Adjustment 2 (e.g., after Load Adjustment 1: adjust torque on reducer 302a with counter-clockwise half turn or Y lbs of pressure decrease).

In various implementations, due to the interrelated nature of the loading across different reduction instruments (e.g., reducers 302a, 302b, etc.), reduction sequencing instructions 360 can include a multi-reducer sequence that in certain cases involves adjusting the load on a given reducer 302 more than once in a complete sequence. For example, the reduction sequencing instructions 360 can include instructions to first adjust the load on a first reducer 302a by an amount that does not fully seat the rod into the anchor receiver, then adjust the load on a second reducer 302b, and subsequently further adjust the load on the first reducer 302 by an amount that fully seats the rod into the anchor receiver.

In particular implementations, e.g., as illustrated in FIG. 12, the spinal fixation system 400 can further include an interface 380 that enables interaction between the reduction feedback system 320 and the surgeon, medical professional (s) and/or other operators in the spinal fixation procedure room. In some cases, the spinal fixation system 400 communicates with the reducer(s) 302 via a communications device 390 such as the wireless and/or hard wired communication devices described herein. The interface(s) 380 can include any conventional visual, tactile and/or auditory interface that can enable communication of reduction feedback information to the surgeon, medical professional and/or operator during the spinal fixation procedure. In certain cases, the interface(s) 380 include a graphical user interface (GUI), which can include a liquid crystal display (LCD), one or more touch screens, virtual medical assistant systems (e.g., voice-based command system), etc. In particular cases, as illustrated in FIGS. 9-11, the interface(s) 380 can include a visual indication system 410 and/a tactile indication system 420 for providing an indicator of the load data 340 (FIG. 13) detected by sensors 308 at the reducer(s) 302. That is, in certain implementations, at least a portion of the visual indication system 410 and/or tactile indication system 420 is located at the reducer 302 (e.g., at each reducer, coupled with housing 316). In additional implementations, a portion of the visual indication system 410 and/or tactile indication system 420 can be located at a centralized interface, e.g., interface 380 at the spinal fixation system 400.

In certain implementations, the tactile indication system 420 includes at least one vibro-tactile actuator, which can be configured to convey to the surgeon (or other medical professional or operator) that a reducer 302 requires further loading and/or is approaching an over-loaded condition. For example, the tactile indication system 420 can be configured to trigger a vibrational cue (e.g., by vibrating the housing 316) when the loading for a given reducer 302 is approaching a maximum absolute loading threshold. In some cases, the tactile indication system 420 can be integrated in housing 316 or otherwise connected with the housing 316 to initiate a vibrational response to the load data from a corresponding sensor 308 approaching and/or exceeding a maximum absolute loading threshold. In additional cases, the tactile indication system 420 is configured to provide distinct vibrational cues of the loading of a reducer, e.g., a first set of vibrational cues indicating under-loading, and a second set of vibrational cues indicating over-loading or approaching a loading limit.

Figure 15:
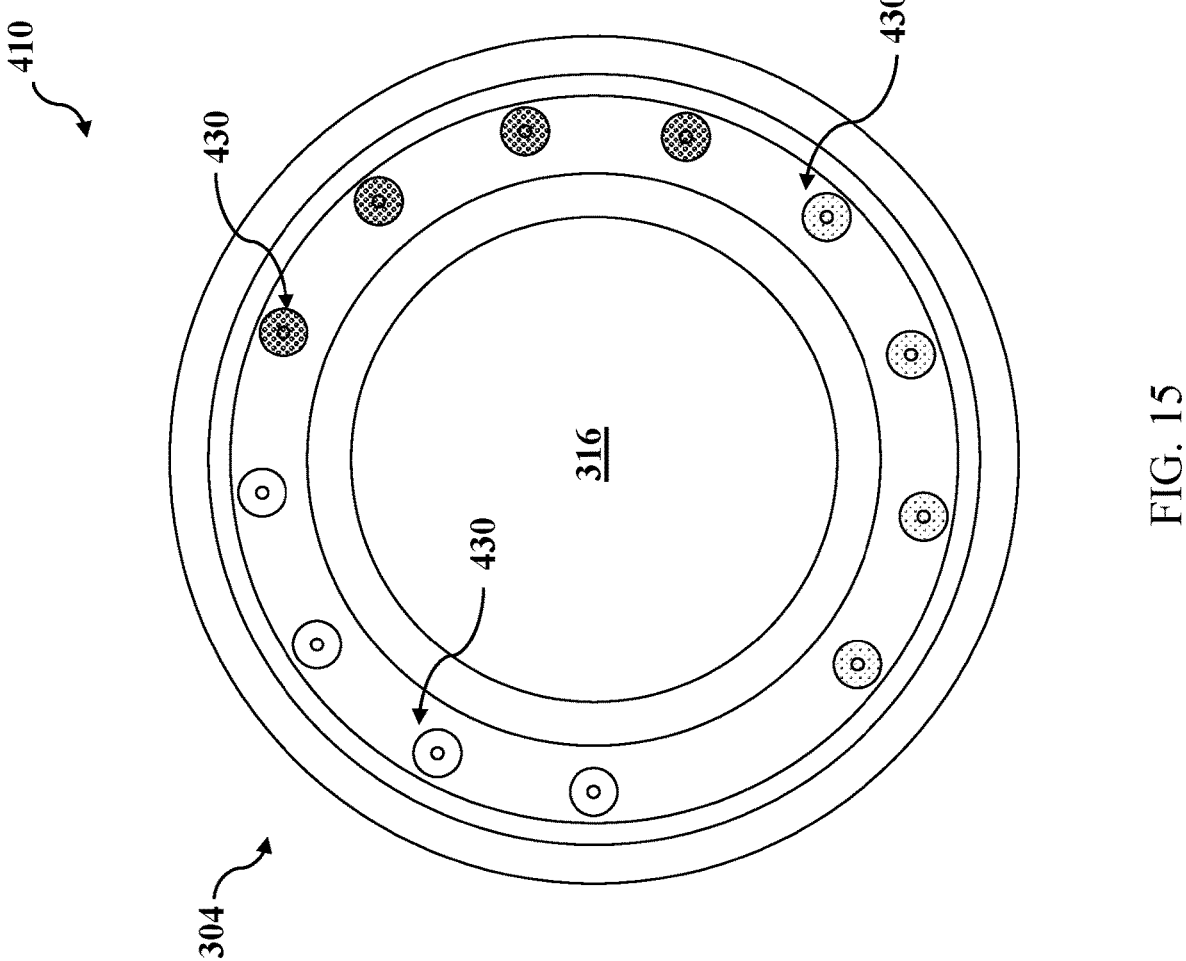
FIG. 15 is a top view of a visual indication mechanism according to various implementations.

FIG. 15 shows an example of a proximal end 304 of a reducer 302 (e.g., proximal end of housing 316) that includes a visual indication system 410 having a set of lights 430 configured to be illuminated in at least two distinct patterns to indicate distinctions in the load data for the reducer 302. This example shows lights 430 of differing colors, but any progressive lighting arrangement can be used to provide the distinct patterns. For example, an annular arrangement of lights 430 as illustrated in FIG. 15 can be configured to provide distinctions in color, e.g., green indicating desired loading, yellow approaching over-loading, red indicating over-loading. In some cases, this annular arrangement of lights 430 has a same or similar color, but can be illuminated in at least two distinct patterns (to indicate over/under loading). An annular lighted arrangement is only one of the various possible arrangements in keeping with the implementations herein, and as such, linear light arrays, light bars, distinctions in light intensity, etc., can be used to visually indicate loading for a given reducer 302.

Figure 16:
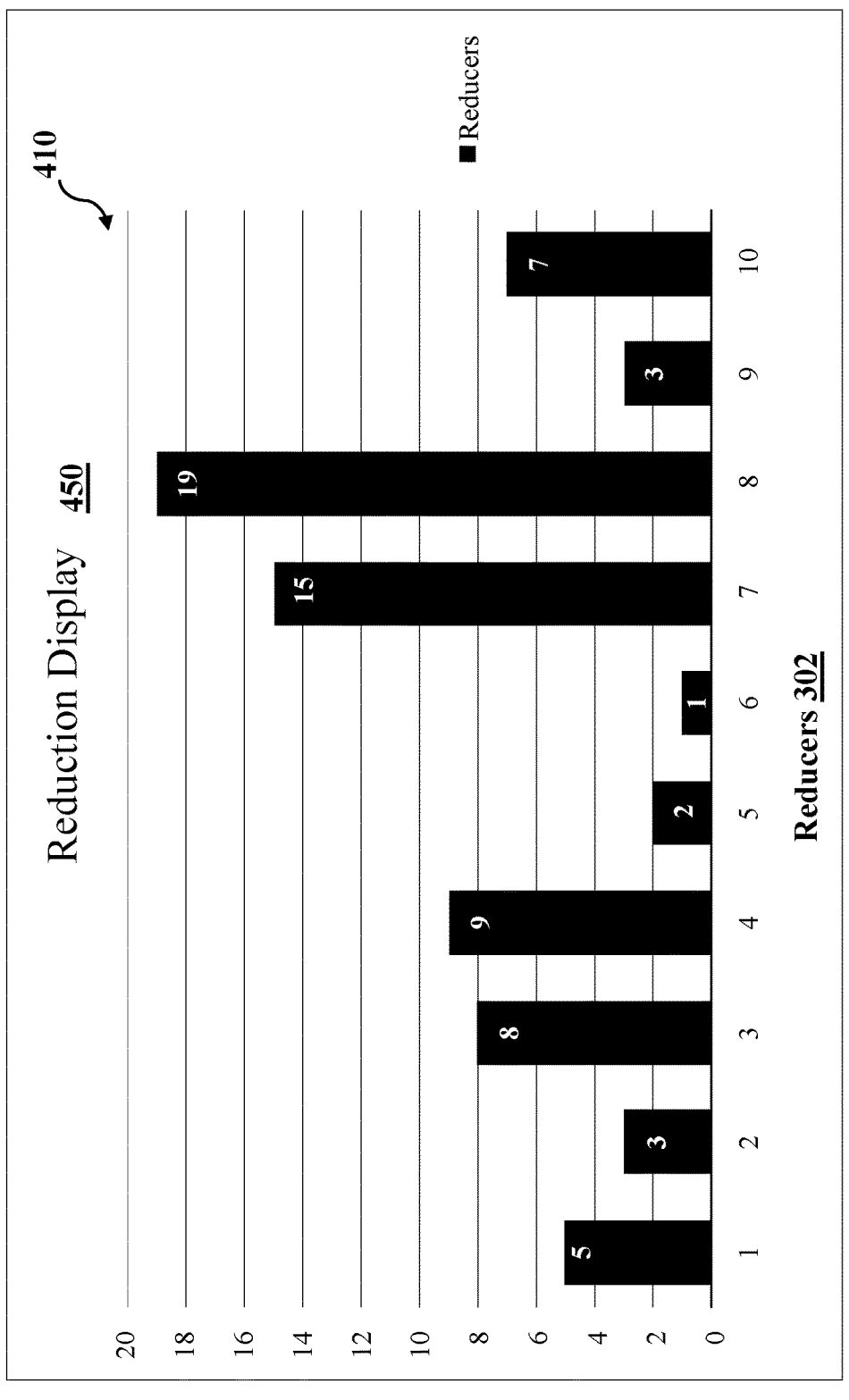
FIG. 16 is a schematic view of a visual indication mechanism according to various additional implementations.

FIG. 16 illustrates another example of a visual indication system 410 (e.g., via interface 380), including for example, a reduction display 450 that includes a bar graph showing load levels (e.g., on a scale of zero to twenty) across a set of ten (10) distinct reducers 302. In this example, the bar graph can be dynamically updated as changes in load data are detected for one or more reducers 302, such that the viewer (e.g., surgeon, medical professional or other operator) can see which reducers 302 are least loaded, or otherwise can withstand increased loading, and which reducer(s) 302 are approaching an upper limit for loading. In certain of these cases, the reduction display 450 can utilize distinctions in color (not shown) to indicate sequencing or otherwise supplement the indication of the least loaded reducer 302, e.g., the first reducer 302 that should undergo an increase in loading.

Returning to FIG. 12, in various additional implementations (illustrated in phantom as optional), the reduction feedback system 320 is further coupled with one or more additional fixation instrument(s) 500, which can include one or more sensors 308, such as the load sensors described herein. In particular cases, the fixation instrument 500 includes a driver configured to tighten a lock screw within a bone anchor receiver (e.g., receiver in bone anchor (e.g., anchor 12 in FIGS. 1-6 and/or pedicle screw 212 in FIGS. 7 and 8), and lock a rod (e.g., rod 14 in FIGS. 1-6 and/or spinal rod 214 in FIGS. 7 and 8) relative to the bone anchor. Examples of such fixation instruments are provided in US Patent Application Publication No. 2020/0297393 (U.S. application Ser. No. 16/898,713), which is incorporated by reference in its entirety. In further particular cases, the fixation instrument 500 includes a guide (also called a "guide tube" in some cases) for defining the trajectory of instruments and/or screws during a spinal surgery. Examples of fixation instruments such as guides and guide tubes are provided in US Patent Application Publication No. 2021/0085485 (U.S. application Ser. No. 16/995,602), which is incorporated by reference in its entirety.

Figure 18:
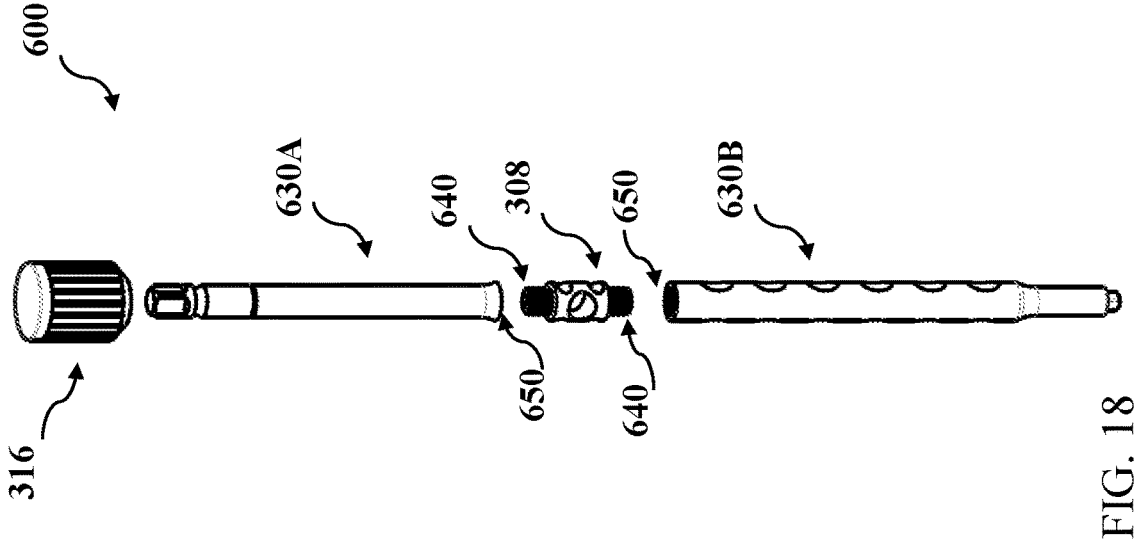
FIG. 18 shows an exploded perspective view of the example driver of FIG. 17, according to various implementations.
Figure 17:
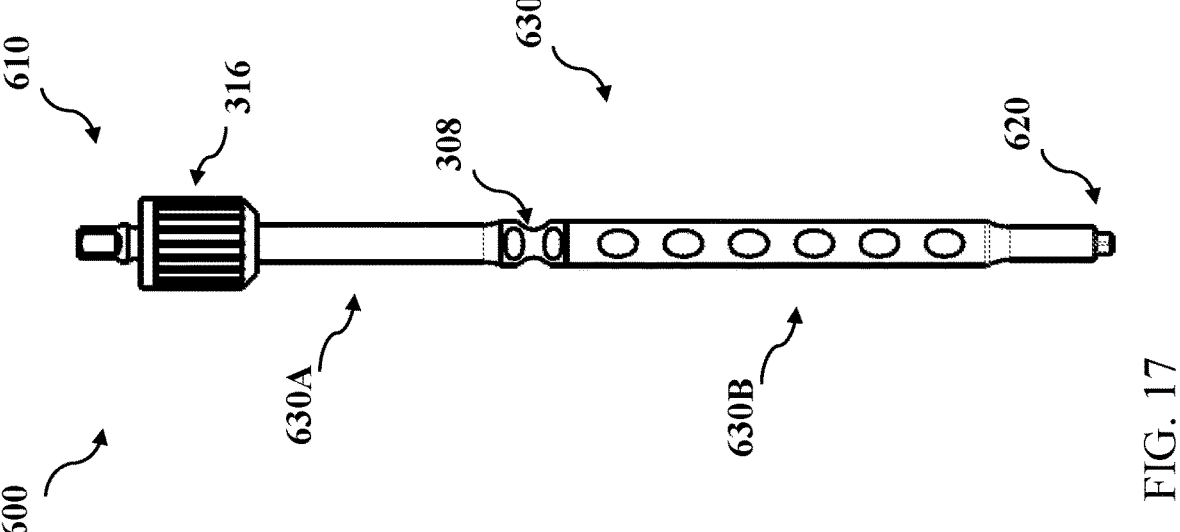
FIG. 17 shows a side view of an example driver according to various implementations.

With reference to additional fixation instruments, FIGS. 17 and 18 illustrate side and exploded perspective views, respectively, of an example of a driver 600 according to various implementations. In this case, the driver 600 has a proximal end 610 and a distal end 620, where the distal end 620 is configured to engage with and tighten a lock screw. A sensor 308 is shown located coaxially with the driver 600, e.g., mounted between or within sections 630A, 630B of the driver shaft 630. In certain cases, the housing for the sensor 308 includes one or more mating features 640 for coupling with complementary mating features 650 in the shaft 630. In certain additional cases, a housing 316 mounted to the shaft 630, e.g., near the proximal end 610, includes one or more additional sensors 308 and/or electronics 318, power source (s) 321, and/or indication systems 410, 420 such as those described with reference to FIGS. 9-11. In the example of the driver 600 depicted in FIGS. 17 and 18, the sensor(s) 308 can be configured to provide torsional force data indicating a torsional force applied on the lock screw during tightening of the lock screw within the receiver, e.g., in the process of locking the rod relative to the bone anchor. In certain cases, the driver (or, driver instrument) 600 is configured to be coupled with the rod reducer(s) 302 described herein. In particular implementations, the driver 600 can be configured to be inserted through the rod reducer 302 to deliver and tighten a lock screw within the receiver to lock the rod relative to the bone anchor. According to certain implementations, the sensor(s) 308 in driver 600 can be configured to provide torsional force data about a torsional force applied by the driver 600 on the lock screw. In some examples, the driver 600 can be deployed as a "finishing" or "final tightening" driver that is configured to tighten the lock screw in its final or finishing phase. In such cases, the sensor(s) 308 in the driver 600 can be configured to provide data about the torsional force applied by the driver 600 on the lock screw in the final or finishing phase.

In still further implementations, the sensor(s) 308 in the fixation instruments 500 (e.g., driver 600, rod reducer 302 and/or a guide tube) described herein, can be configured to provide data about a load exerted by the fixation instrument 500 on the rod during seating of the rod into the receiver of the bone anchor, and/or data about a tensile load between the rod and the bone anchor when the rod is at least partially seated within the bone anchor. In certain implementations, both torque and compression data are recorded by sensor(s) 308 on fixation instruments 500 and provided to the reduction feedback system 320 for analysis and/or action (e.g., to adjust reduction instructions). It is understood that torque and/or compression data detected by sensors 308, e.g., such as in a sensor mounted to the driver 600 and/or rod reducer 302, can represent an inferred or correlated indicator of the torque and/or compression applied to a device or component not physically in contact with the sensor 308. For example, the sensor 308 on an instrument 500 (e.g., driver 600) can be configured to detect torque at the instrument 500, while that torque is being translated to a lock screw in contact with the distal end of the instrument. Similarly, the sensor 308 on an instrument 500 (e.g., rod reducer 302) can detect compression at the instrument 500, while that compression is being translated to a rod.

In additional implementations, one or more fixation instruments described herein, e.g., rod reducers 302, fixation instrument(s) 500, etc. can be communicatively coupled with a navigation system (e.g., via spinal fixation system 400) that is configured to detect a position of the instrument (s). In one example depiction in FIG. 12, a navigation system 700 (indicated in phantom as optional) is coupled with the reduction feedback system 320 in order to provide navigation information about a position of instruments. For example, the navigation system 700 can include an optical tracking system such as a camera or laser-based tracking system, a Global Positioning System (GPS), an inertial measurement unit (IMU), etc. In certain cases, the navigation system 700 is configured to determine a distance moved by the instrument when the instrument changes position, which the navigation system 700 communicates to the reduction feedback system 400. One or more components of a navigation system 700 can be located within or otherwise integrated with a housing, e.g., housing 316 (FIGS. 9-11), that is mounted to or otherwise coupled with one or more of the reduction instruments. For example, components of a navigation system such as a GPS and/or IMU can be located in a housing 316. In certain examples, the navigation system 700 and/or a portion thereof is fixed to a portion of the rod reducer(s) 302, fixation instrument(s) 500, etc., and is physically separated from the housing 316. In some of these cases, e.g., where the housing 316 and/or other electronics packages are modular, the navigation system 700 can remain independently coupled to the rod reducer 302, fixation instrument 500 or other instrument. In additional implementations, the spinal fixation system 400 includes or is coupled with a navigation system 700 that is external to the housing 316 and/or the reduction instruments.

With reference to FIGS. 12 and 13, in additional implementations, the reduction feedback system 320 is configured to provide post-operative data and analysis of reduction procedure and/or device usage, e.g., to enhance future procedures and/or diagnose inefficiencies in a past procedure. In certain implementations, the reduction feedback system 320 is configured to update the RF instructions 328 based on identified inefficiencies or errors in reduction sequencing and/or device usage during a given procedure. In particular implementations, the reduction feedback system 320 includes a logic engine configured to modify RF instructions 328 iteratively, e.g., on a procedure-by-procedure basis.

As noted herein, the reduction devices, reduction feedback systems and spinal fixation systems disclosed according to various implementations provide numerous benefits relative to conventional spinal fixation devices and systems. For example, the disclosed devices, systems, feedback systems, and methods can enhance efficacy of spinal fixation procedures, as well as mitigate operator (e.g., surgeon) error in performing such procedures. Various disclosed implementations can improve patient outcomes when compared with conventional spinal fixation procedures. Additionally, the disclosed implementations can provide real-time and/or post-operative feedback on reduction procedures, enhancing both current procedural outcomes as well as future surgical outcomes. In certain implementations, the reduction feedback system can provide information to an operator regarding desired reduction ordering in a multi-level reduction procedure, thereby mitigating or avoiding overloading of instruments at any given time during the procedure.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

In various implementations, components described as being "coupled" to one another can be joined along one or more interfaces. In some implementations, these interfaces can include junctions between distinct components, and in other cases, these interfaces can include a solidly and/or integrally formed interconnection. That is, in some cases, components that are "coupled" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" can be linked via conventional hard-wired and/or wireless means such that these electronic components can communicate data with one another. Additionally, sub-components within a given component can be considered to be linked via conventional pathways, which may not necessarily be illustrated.

While inventive features described herein have been described in terms of preferred embodiments for achieving the objectives, it will be appreciated by those skilled in the art that variations may be accomplished in view of these teachings without deviating from the spirit or scope of the invention. Also, while this invention has been described according to a preferred use in spinal applications, it will be appreciated that it may be applied to various other uses desiring surgical fixation, for example, the fixation of long bones.

A number of implementations have been described. Nevertheless, it will be understood that additional modifications may be made without departing from the scope of the inventive concepts described herein, and, accordingly, other implementations are within the scope of the following claims.

We claim:

1. A spinal fixation system, comprising:
    a first bone anchor including a first pedicle screw and a receiver;

a rod configured to be seated within the receiver of the first bone anchor;

an instrument configured to couple to the first bone anchor, the instrument having a multi-section shaft; and a sensor mounted axially between distinct sections of the multi-section shaft and configured to determine data relating to at least one of: the first bone anchor, the rod or the instrument a reduction feedback system coupled with the sensor, the reduction feedback system configured to:

receive load data indicating the load exerted by the rod reducer instrument on the portion of the spinal rod from a corresponding one of the sensors;

provide an indicator of relative loading of the instrument as compared with at least one additional rod reducer instrument in the plurality of rod reduction instruments, and update the indicator of relative loading over time as load data for at least one of the first rod reducer or the additional rod reducers in the plurality of rod reduction instruments is updated, wherein the reduction feedback system is further configured to:

compare the load data for each of the rod reducers instruments with a corresponding load threshold; and for each of the rod reducers instruments: provide an indicator that the load data satisfies or does not satisfy the load threshold for the rod reducer, the indicator being detectable by an operator of the plurality of rod reduction instruments, wherein the load threshold for the rod reducer is based at least in part on a model that correlates clinical data representing patient-specific bone quality with screw pullout.

2. The spinal fixation system of claim 1, wherein the instrument is configured to seat the rod in the receiver of the first bone anchor, and wherein sensor is configured to determine the load data during seating of the rod in the receiver.

3. The spinal fixation system of claim 1, wherein the multi-section shaft is a multi-section driver shaft.

4. The spinal fixation system of claim 1, further comprising a housing that houses the sensor and includes at least one mating feature coupled with a complementary mating feature on the multi-section shaft.

5. The spinal fixation system of claim 1, wherein a distal end of the instrument is configured to engage with and tighten a lock screw.

6. The spinal fixation system of claim 5, wherein the sensor is configured to provide torsional force data about a torsional force applied by the instrument on the lock screw.

7. The spinal fixation system of claim 6, wherein the multi-section shaft is part of a finishing driver for providing finishing tightening on the lock screw, and wherein the sensor is configured to provide data about the torsional force applied to the lock screw in the finishing tightening phase.

8. The spinal fixation system of claim 1, wherein the sensor is configured to provide torque data and compression data relating to at least one of: the first bone anchor, the rod or the instrument.

9. The spinal fixation system of claim 1, wherein the instrument further comprises an interface for providing an indicator of relative loading of the instrument as compared with a set of additional instruments coupled with the rod.

10. A spinal fixation monitoring system for use in a spinal fixation procedure, the system comprising:

a plurality of rod reduction instruments adapted for use with a spinal fixation system, each of the rod reduction instruments including:

a rod reducer having a proximal end and a distal end, wherein the distal end of the rod reducer is configured to engage a spinal rod for seating the spinal rod into a corresponding pedicle screw receiver; and a sensor configured to detect a load exerted by the rod reducer on a portion of the spinal rod during seating of the spinal rod in the pedicle screw receiver; and a reduction feedback system coupled with the sensor of each of the rod reduction instruments, the reduction feedback system configured to:

receive load data indicating the load exerted by each rod reducer on the portion of the spinal rod from a corresponding one of the sensors;

provide an indicator of relative loading of a first rod reducer as compared with at least one additional rod reducer in the plurality of rod reduction instruments, and update the indicator of relative loading over time as load data for at least one of the first rod reducer or the additional rod reducers in the plurality of rod reduction instruments is updated, wherein the reduction feedback system is further configured to:

compare the load data for each of the rod reducers with a corresponding load threshold; and for each of the rod reducers: provide an indicator that the load data satisfies or does not satisfy the load threshold for the rod reducer, the indicator being detectable by an operator of the plurality of rod reduction instruments, wherein the load threshold for the rod reducer is based at least in part on a model that correlates clinical data representing patient-specific bone quality with screw pullout.

11. The system of claim 10, wherein the indicator of relative loading indicates whether the first rod reducer is more loaded, less loaded, or equally loaded relative to the additional rod reducers in the plurality of rod reduction instruments.

12. The system of claim 10, wherein the load threshold defines a maximum acceptable load exerted by the rod reducer on the spinal rod during seating of the spinal rod in the pedicle screw receiver.

13. The system of claim 10, wherein the model is updateable based on updates to the clinical data.

14. The system of claim 10, wherein the reduction feedback system comprises a housing mounted to the proximal end of each of the rod reducers for providing the indicator of the load data proximate to each of the rod reducers.

15. The system of claim 14, wherein the housing is at least one of modular or disposable.

16. The system of claim 10, wherein the indicator of reduction order includes reduction instructions for multi-step reduction of the plurality of rod reduction instruments.

17. A spinal fixation monitoring system for use in a spinal fixation procedure, the system comprising:

a plurality of rod reduction instruments adapted for use with a spinal fixation system, each of the rod reduction instruments including:

a rod reducer having a proximal end and a distal end, wherein the distal end of the rod reducer is configured to engage a spinal rod for seating the spinal rod into a corresponding pedicle screw receiver; and

US 12,594,099 B2

21 a sensor configured to detect a load exerted by the rod
  reducer on a portion of the spinal rod during seating
  of the spinal rod in the pedicle screw receiver; and
a reduction feedback system coupled with the sensor of
  each of the rod reduction instruments, the reduction
  feedback system configured to:
receive load data indicating the load exerted by each
  rod reducer on the portion of the spinal rod from a
  corresponding one of the sensors;
provide an indicator of relative loading of a first rod
  reducer as compared with at least one additional rod
  reducer in the plurality of rod reduction instruments,
  and
update the indicator of relative loading over time as
  load data for at least one of the first rod reducer or the
  additional rod reducers in the plurality of rod reduc-
  tion instruments is updated,
wherein the reduction feedback system is further con-
  figured to provide an indicator of reduction order for
  the plurality of rod reduction instruments based on
  the received load data.

\* \* \* \* \*